United States Patent
Sakane

(10) Patent No.: US 12,377,418 B2
(45) Date of Patent: Aug. 5, 2025

(54) MEDICAL CONTAINER

(71) Applicant: JMS CO., LTD., Hiroshima (JP)

(72) Inventor: Hiroto Sakane, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 830 days.

(21) Appl. No.: 17/618,627

(22) PCT Filed: Jun. 11, 2020

(86) PCT No.: PCT/JP2020/023070
§ 371 (c)(1),
(2) Date: Dec. 13, 2021

(87) PCT Pub. No.: WO2020/250988
PCT Pub. Date: Dec. 17, 2020

(65) Prior Publication Data
US 2022/0234047 A1    Jul. 28, 2022

(30) Foreign Application Priority Data

Jun. 11, 2019 (JP) ................................ 2019-108624
Mar. 17, 2020 (JP) ................................ 2020-046360

(51) Int. Cl.
*B01L 9/06* (2006.01)
*B65D 33/10* (2006.01)

(52) U.S. Cl.
CPC ................. *B01L 9/06* (2013.01); *B65D 33/10* (2013.01); *B01L 2200/141* (2013.01); *B01L 2300/123* (2013.01)

(58) Field of Classification Search
CPC ................. B01L 9/06; B01L 2200/141; B01L 2300/123; B65D 33/10; B65D 2050/3006;
(Continued)

(56) References Cited

U.S. PATENT DOCUMENTS 5,997,811 A    12/1999  Esposito
2012/0202000 A1  8/2012  Bricker et al.
(Continued)

FOREIGN PATENT DOCUMENTS

JP    2002-337888 A    11/2002
JP    2010-17484 A     1/2010
(Continued)

OTHER PUBLICATIONS

An Office Action in corresponding JP Application No. 2020-046360 mailed Oct. 3, 2023 and its English machine translation are attached, 3 and 5 pages respectively.

*Primary Examiner* — Jill A Warden
*Assistant Examiner* — Michael Stanley Gzybowski
(74) *Attorney, Agent, or Firm* — MUNCY, GEISSLER, OLDS & LOWE, P.C.

(57) ABSTRACT

Provided is a medical container from which an accommodated object is easily extracted without being contaminated. A medical container 1 formed by joining together rims of a set of sheet-shaped members 50 and 50 disposed facing each other is provided with: an accommodation part 10 that is disposed at a central part in a width direction WD; and a pair of extending parts 20 that is disposed on one end side in a height direction HD of the accommodation part 10 and extends outward in the width direction from the accommodation part 10. The medical container 1 is preferably provided with partition joining parts 30 that extend from the other end side to the one end side in the height direction HD and partition the accommodation part 10 and the extending parts 20 at boundary portions between the accommodation part 10 and a pair of the extending parts 20.

8 Claims, 14 Drawing Sheets

(58) Field of Classification Search
CPC ... A61B 50/20; A61B 2050/314; A61B 50/30; A61J 1/00; A61J 1/10
See application file for complete search history.

(56) References Cited

U.S. PATENT DOCUMENTS

2012/0205269 A1   8/2012   Ludvig
2013/0066292 A1   3/2013   Ueda
2013/0202483 A1   8/2013   Tennican

FOREIGN PATENT DOCUMENTS

| JP | 2011-078737 A | 4/2011 |
| JP | 2014-510567 A | 5/2014 |
| JP | 2015-509386 A | 3/2015 |
| JP | 2015-227177 A | 12/2015 |
| JP | 2019-26271 A | 2/2019 |
| WO | WO2012/066865 A1 | 5/2012 |
| WO | WO 2012/104811 A1 | 8/2012 |
| WO | WO 2013/119505 A1 | 8/2013 |
| WO | WO 2014/076819 A1 | 5/2014 |

…

MEDICAL CONTAINER

TECHNICAL FIELD

The present invention relates to a medical container.

BACKGROUND ART

Conventionally, instruments and pharmaceutical preparations used for medical treatment are stored and transported in a sealed state by a resin container for protection from the outside world and prevention of contamination (see, for example, Patent Document 1). When an accommodated object such as these instruments and pharmaceutical preparations are used, the container is opened by a person in charge of an unclean field in an operating room where the unclean field and a clean field are separated, and the accommodated object is extracted from the container by a person in charge of the clean field.

Patent Document 1: Japanese Unexamined Patent Application (Translation of PCT Application), Publication No. 2015-509386

DISCLOSURE OF THE INVENTION

Problems to be Solved by the Invention

Herein, the outside of the container is classified in the unclean field because the outside of the container is in contact with the outside world. It is also considered that an opening, which is an opening portion of the container, is also contaminated. Therefore, it is desirable to extract the accommodated object from the container without touching the opening.

Therefore, an object of the present invention is to provide a medical container from which an accommodated object is easily extracted without being contaminated.

Means for Solving the Problems

The present invention relates to a medical container provided by joining together rims of a set of sheet-shaped members disposed facing each other, the medical container including: an accommodation part disposed at a central part in a width direction; and a pair of extending parts that is disposed on one end side in a height direction of the accommodation part, and extends outward in the width direction from the accommodation part.

The medical container preferably further includes an accommodating opening provided in a portion of the rims.

The medical container preferably further includes partition joining parts that extend from the other end side to the one end side in the height direction, and partition the accommodation part and the extending parts at boundary portions between the accommodation part and a pair of the extending parts.

A position of an end portion on the one end side in the height direction of each of the partition joining parts is preferably located on the other end side with respect to one end portion in the height direction of an accommodated object in a state in which the accommodated object is accommodated in the accommodation part.

The medical container preferably further includes a regulating joining part that regulates a position of an accommodated object accommodated in the accommodation part, in the accommodation part.

The medical container preferably further includes a regulating joining part that regulates a position of an accommodated object accommodated in the accommodation part, in the accommodation part, wherein the accommodating opening is preferably provided at an edge on a side where the regulating joining part is disposed in the accommodation part.

A length in the height direction of each of the extending parts is preferably shorter than a length in the height direction of the accommodation part.

A side on the other end side in the height direction of each of the extending parts is preferably inclined on the one end side in the height direction from an end portion in the width direction toward the accommodation part.

The present invention relates to a medical container provided by joining together rims of a set of sheet-shaped members disposed facing each other, the medical container including: an accommodation part disposed at a central part in a width direction; an inclined part disposed on an upper end side in a height direction of the accommodation part; and a rectangular part disposed on an upper end side in the height direction of the inclined part, wherein the inclined part is configured to gradually decrease a width from the upper end side toward a lower end side, the rectangular part has a width larger than a width of the accommodation part, a distance a in the width direction between an end portion of an upper end portion of the accommodation part and an end portion of an upper end portion of the inclined part is 35 mm or more and 70 mm or less, and a distance b in the height direction between the upper end portion of the accommodation part and the upper end portion of the inclined part is 20 mm or more and 40 mm or less.

A width d of the upper end portion of the accommodation part is not preferably more than the distance a.

A width c of the upper end portion of the inclined part is preferably 200 mm or less.

An angle $\theta 2$ on an acute angle side with respect to the width direction of a lateral side of the inclined part is preferably 20° or more and 40° or less.

Effects of the Invention

According to a medical container of the present invention, an accommodated object can be easily extracted without being contaminated.

PREFERRED MODE FOR CARRYING OUT THE INVENTION

Hereinafter, preferred embodiments of a medical container of the present invention will be described with reference to the drawings. First, a configuration of the medical container of the first embodiment will be described with reference to FIG. 1 to FIG. 3. The medical container is used to accommodate an instrument, a pharmaceutical preparation, or the like used for medical treatment as an accommodated object, and to protect the accommodated object from contamination to maintain hygiene. A medical container 1 of the first embodiment accommodates an accommodating container 60 that accommodates, as an accommodated object, cells used for regenerative medicine, or the like.

Figure 1:
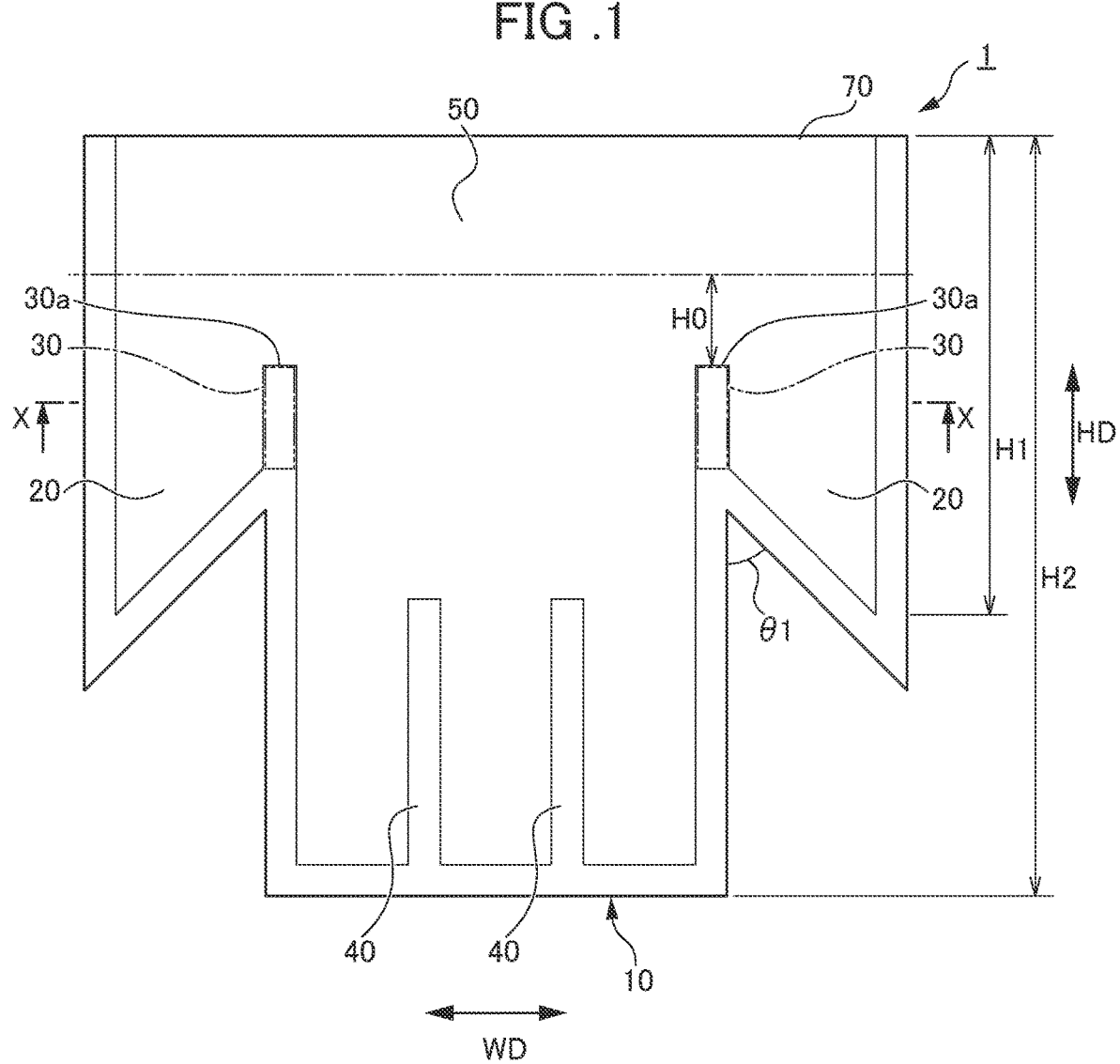
FIG. 1 is a plan view illustrating a medical container according to a first embodiment of the present invention.
Figure 2:
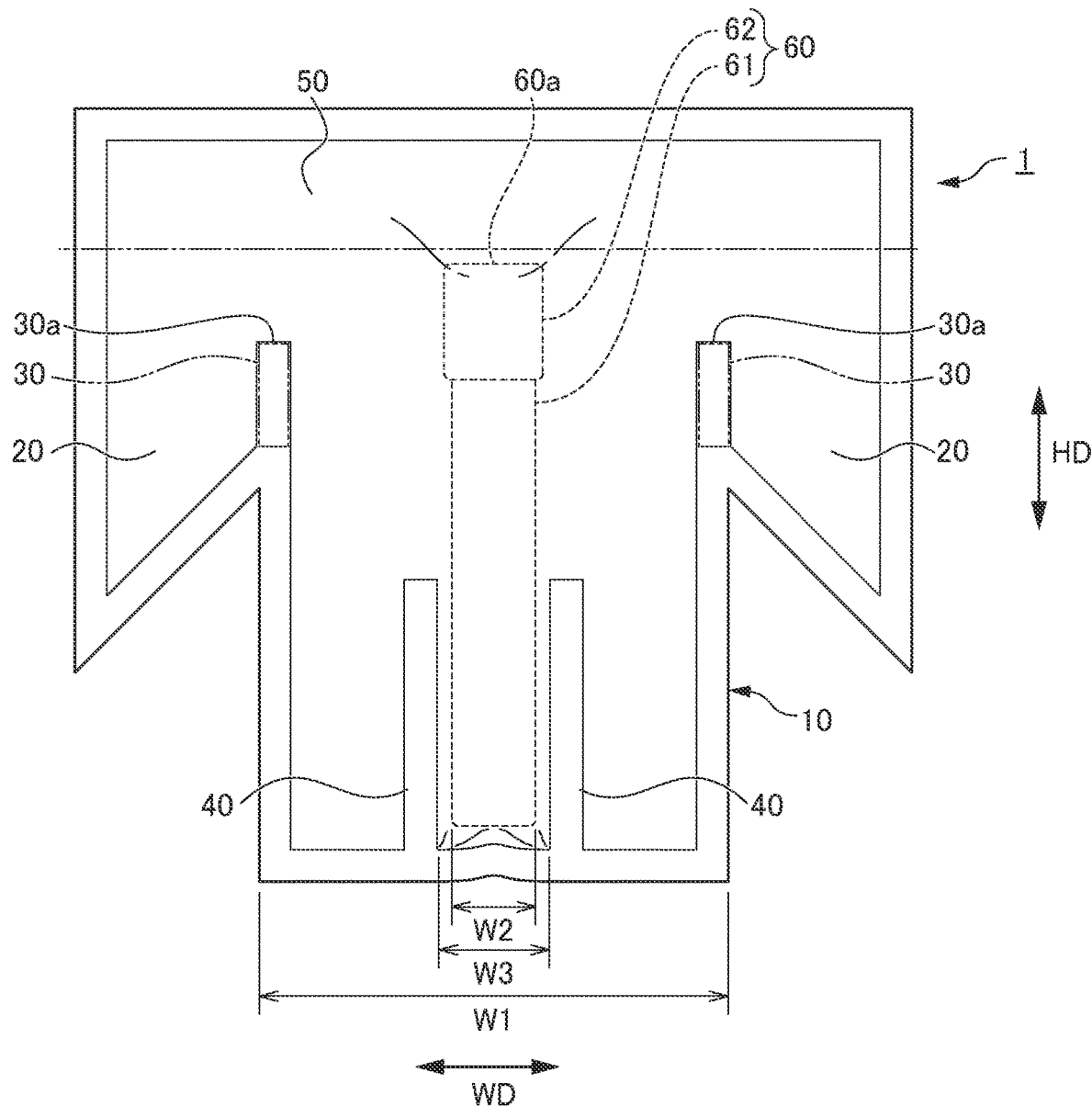
FIG. 2 is a plan view illustrating a state in which an accommodated object is accommodated in the medical container according to the first embodiment.
Figure 3:
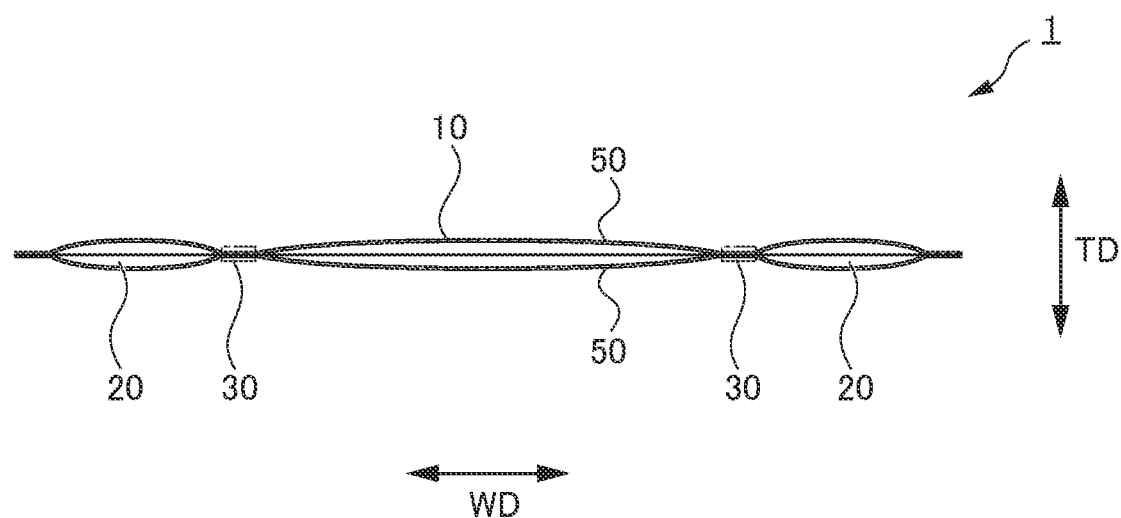
FIG. 3 is a cross-sectional view taken along a line X-X of FIG. 1.

As illustrated in FIG. 1 to FIG. 3, the medical container 1 is formed in a bag shape by joining together rims of a set (two) of sheet-shaped members 50 and 50 disposed (see FIG. 3) facing each other by heat sealing or ultrasonic joining except an accommodating opening 70 (upper side portion in FIG. 1) for accommodating an accommodated object. The sheet-shaped members 50 are made of flexible thermoplastic resin. Examples of the material constituting the sheet-shaped members include EVA resin (ethylene-vinyl acetate copolymer resin), polyolefins such as polyethylene and polypropylene, and vinyl chloride. In the present embodiment, the sheet-shaped members 50 are made of EVA resin. The sheet-shaped members 50 are made of EVA resin, so that even when the medical container 1 is cryopreserved, the flexibility can be maintained, and the medical container 1 can be prevented from being damaged at a low temperature.

As illustrated in FIG. 1 to FIG. 3, the medical container 1 includes an accommodation part 10, a pair of the extending parts 20, a pair of partition joining parts 30, regulating joining parts 40, and the accommodating opening 70.

As illustrated in FIG. 1 and FIG. 2, the accommodation part 10 is formed in a rectangular shape in which the length in the width direction WD is shorter than the length in the height direction HD, and is disposed at a central part in the width direction WD of the medical container 1. The accommodation part 10 accommodates, as an accommodated object, an instrument, a pharmaceutical preparation, or the like used for medical treatment in a sterile state. In the present embodiment, as illustrated in FIG. 2, the accommodation part 10 accommodates a cylindrical accommodating container 60 that accommodates cells used for regenerative medicine. The accommodating container 60 includes a cylindrical main body 61 having an open one end side and a cap 62 detachably attached to the main body 61, and the cap 62 is accommodated in the accommodation part 10 so as to be located on the upper end side of the medical container 1 which is one end side in the height direction HD of the medical container 1. In the present embodiment, as illustrated in FIG. 2, the length W1 in the width direction WD of the accommodation part 10 is configured to be larger than the width W2 in the accommodating container 60.

In this specification, the direction in which the accommodation part 10 and a pair of the extending parts 20 are lined up (the horizontal direction in FIG. 1) is defined as the width direction WD of the medical container 1, the direction that intersects the width direction WD and is along the plane direction of the sheet-shaped members 50 (vertical direction in FIG. 1) is defined as the height direction HD, and the overlapping direction of a set of the sheet-shaped members 50 and 50 (vertical direction in FIG. 3) is defined as the thickness direction TD.

The pair of extending parts 20 extends outward in the width direction WD from the accommodation part 10. In each of the extending parts 20, a set of the sheet-shaped members 50 is joined together at a lateral side along the height direction HD, and a base side which is a side on the other end side in the height direction HD, and a set of the sheet-shaped members 50 is not joined together at other portions. Each extending part 20 is disposed on the one end side in the height direction HD of the accommodation part 10. As illustrated in FIG. 1, the length H1 in the height direction HD of the extending part 20 is configured to be shorter than the length H2 of the accommodation part 10 in the height direction HD. Further, the base side of the extending part 20 is inclined on one end side in the height direction HD from an end portion in the width direction WD toward the accommodation part 10 toward. That is, the base side of the extending part 20 is formed in a straight line that is inclined upward from the end portion in the width direction WD toward the accommodation part 10.

The angle θ1 formed by the base side of the extending part 20 and the lateral side along the height direction HD of the accommodation part 10 is preferably 0° to 90°.

A pair of the partition joining parts 30 is formed by joining together a set of the sheet-shaped members 50, and extends from the other end side to the one end side in the height direction HD of the medical container 1, and partition the accommodation part 10 and the extending parts 20 at boundary portions between the accommodation part 10 and a pair of the extending parts 20. In the present embodiment, the partition joining parts 30 are provided such that the lateral sides along the height direction HD of the accommodation part 10 extends to one end side (upper end side).

That is, the partition joining parts 30 are disposed on extension lines of the sides along the height direction HD of the accommodation part 10. The partition joining parts 30 do not completely partition the accommodation part 10 and a pair of the extending parts 20, but partially partition the accommodation part 10 and a pair of the extending parts 20. That is, the accommodation part 10 and the extending parts 20 have communicating portions on the one end side (upper end side) in the height direction HD.

A position 30a of an end portion on the one end side (upper end side) in the height direction HD of each partition joining part 30 is located on the other end side (lower end side) with respect to one end portion (upper end portion) 60a in the height direction HD of the accommodating container 60 in a state in which the accommodating container 60 is accommodated in the accommodation part 10 (see FIG. 2). Further, the length H0 from the position 30a of the end portion on the one end side (upper end side) in the height direction HD of each partition joining part 30 to the opening for extraction of the medical container 1 is made to be an appropriate dimension (length), so that the sheet-shaped members 50, which will be described later, can be easily inverted.

The regulating joining parts 40 are formed by joining together a set of the sheet-shaped members 50, and regulate the position of the accommodating container 60 accommodated in the accommodation part 10. In the present embodiment, the regulating joining parts 40 are formed by two joining parts linearly extending in the height direction HD at a predetermined interval in the width direction WD at the central part in the width direction WD of the accommodation part 10. Further, the regulating joining parts 40 are each provided so as to extend from the base side which is the side on the other end side in the height direction HD of the accommodation part 10 by a predetermined height. The length W3 in the width direction WD between the two joining parts constituting the regulating joining parts 40 is set to be slightly larger than the size (width) W2 of the accommodating container 60.

The accommodating opening 70 is formed without joining together a part of the rims of a set of the sheet-shaped members 50. In the first embodiment, the accommodating opening 70 is provided over the entire length of the side on the one end side (upper end side) in the height direction.

The medical container 1 of the first embodiment described above is used as follows. When the accommodating container 60 is accommodated in the medical container 1, the accommodating container 60 accommodating cells is accommodated, from the accommodating opening 70, in the medical container 1 in which all sides except an upper side, which is a side on the one end side in the height direction HD and is provided with the accommodating opening 70, are joined together. Herein, the accommodating container 60 is inserted between the two joining parts constituting the regulating joining parts 40 such that the cap 62 is located on the upper end side, and is accommodated in a state of being positioned in the accommodation part 10. Thereafter, the upper side of the medical container 1 is joined together, and the accommodating container 60 is accommodated in the medical container 1 in a sealed state. In this state, the upper end portion 60a of the accommodating container 60 is located on the upper end side with respect to the upper end portions 30a of the partition joining parts 30 (see FIG. 2).

The cells accommodated in the accommodating container 60 are accommodated in the medical container 1 and cryopreserved in a sealed state until the cells are used. Herein, the medical container 1 is made of EVA resin, so that even when the medical container 1 is cryopreserved, flexibility can be maintained, and the medical container 1 can be prevented from being damaged at a low temperature.

When the cells accommodated in the accommodating container 60 are used, the cells are transported to an operating room or the like in which an unclean field and a clean field are separated, in a state in which the cells are accommodated in the medical container 1. Then, the medical container 1 is opened by a person in charge of the unclean field, and the accommodating container 60 is extracted from the medical container 1 by a person in charge of the clean field.

Figure 4:
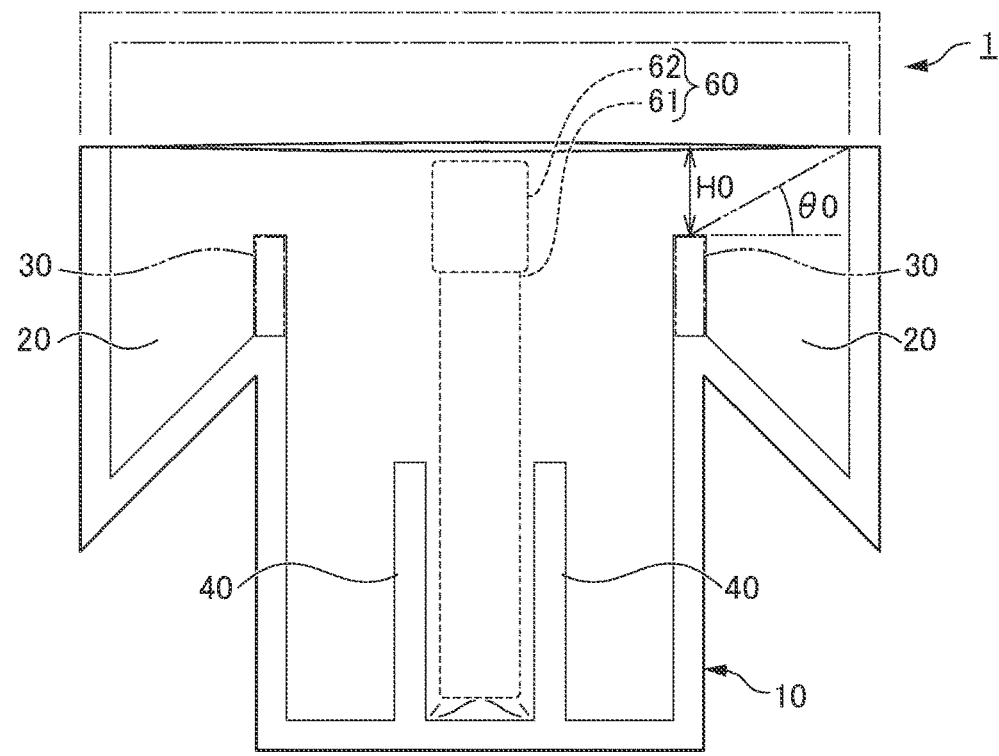
FIG. 4 is a diagram illustrating a method of using the medical container according to the first embodiment, and is a diagram illustrating a state in which an upper end portion of the medical container is cut and opened.

A procedure for extracting the accommodating container 60 from the medical container 1 will be described with reference to FIG. 4 to FIG. 6. First, as illustrated in FIG. 4, the person in charge of the unclean field cuts the upper side of the medical container 1 with scissors or the like. Consequently, an opening for extraction is provided on the upper side of the medical container 1. Herein, the cutting position on the upper side of the medical container 1 is preferably such a position that an angle θ0 (see FIG. 4) formed by the upper end portion 30a of each partition joining part 30 and the end portion of the opening for extraction is 90° to 160° after cutting, and more preferably such a position that the angle θ0 is 100° to 140°.

Figure 5:
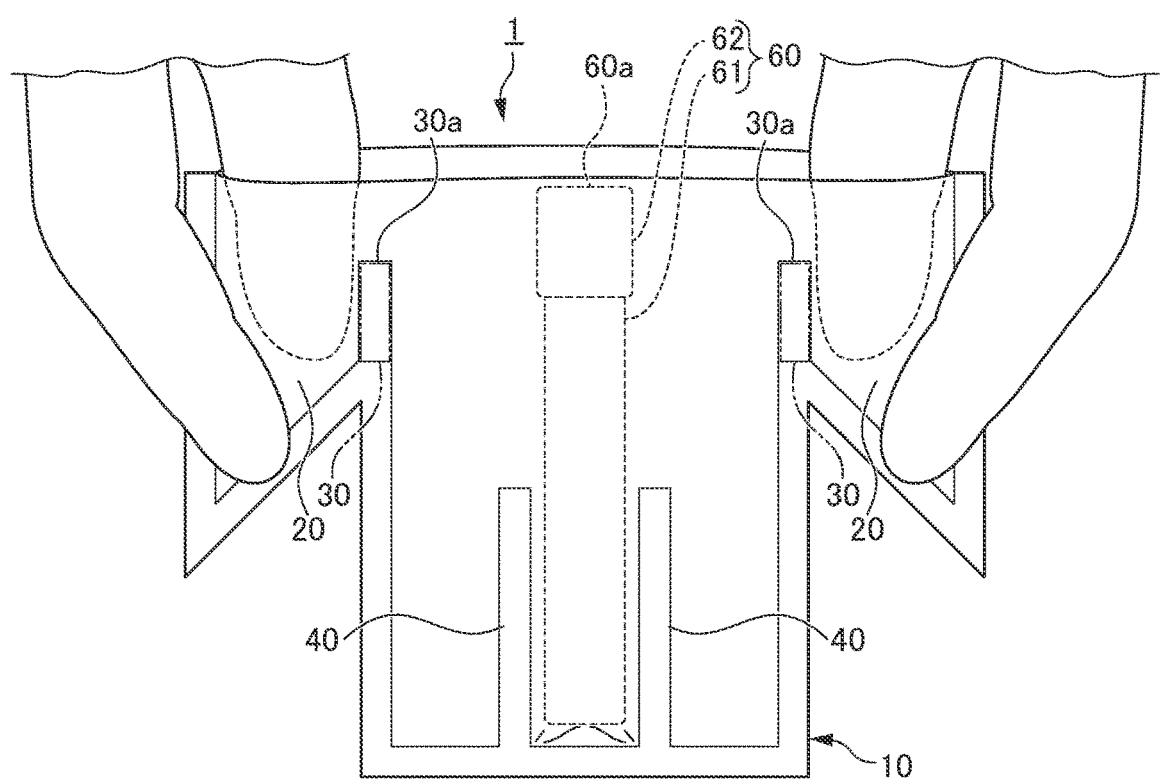
FIG. 5 is a diagram illustrating a method of using the medical container according to the first embodiment, and is a diagram illustrating a state of holding a pair of extending parts.

Then, as illustrated in FIG. 5, a pair of the extending parts 20 are held by the person in charge of the unclean field. Herein, in a pair of the extending parts 20, a set of the sheet-shaped members 50 is not joined together except for the rim parts (lateral sides and bottom sides), and therefore the person in charge of the unclean field inserts, for example, his/her thumbs into a pair of the extending parts 20 from the opening, and sandwiches a sheet of the sheet-shaped member 50 between the inserted thumbs and his/her forefingers, so that it is possible to hold the extending parts 20. Further, the partition joining parts 30 are disposed between the extending parts 20 and the accommodation part 10, and therefore when the extending parts 20 are held, it is possible to prevent the fingers of the person in charge of the unclean field from entering the accommodation part 10 side.

Figure 6:
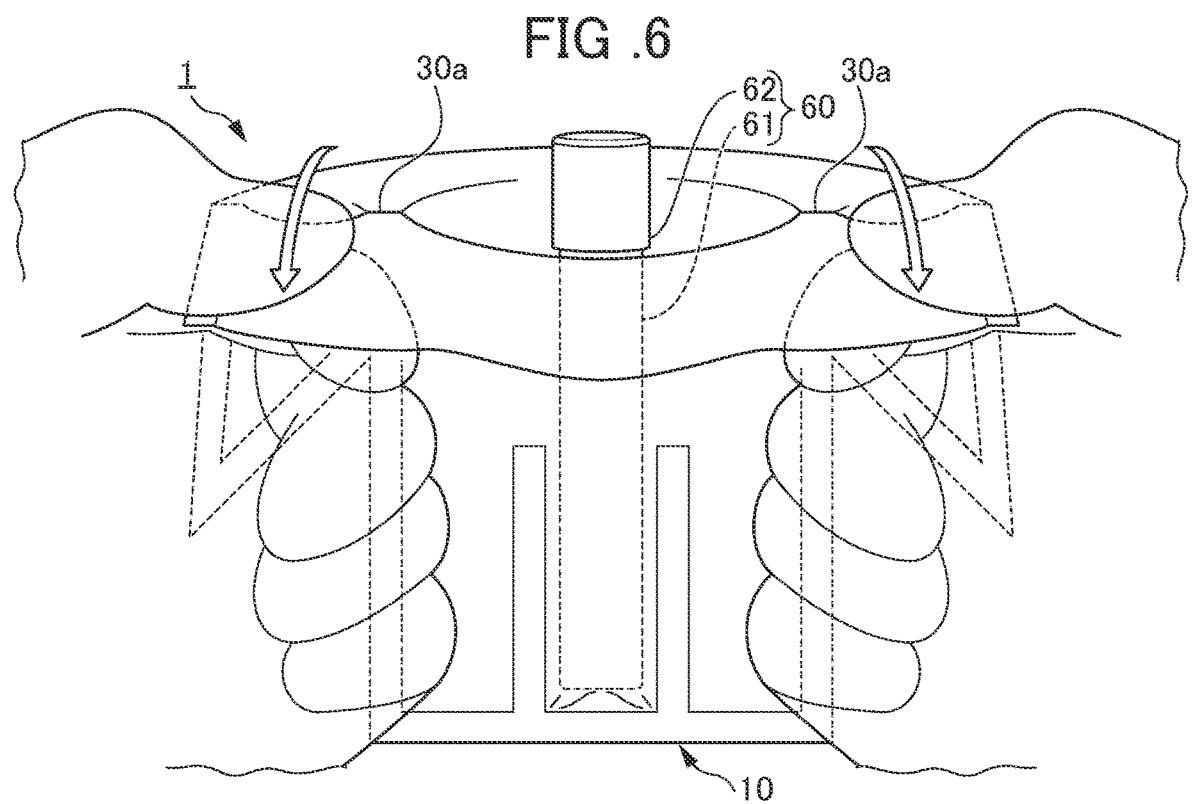
FIG. 6 is a diagram illustrating a method of using the medical container according to the first embodiment, and is a diagram illustrating a state in which a set of sheet-shaped members is inverted at an opening while holding a pair of the extending parts.

Then, as illustrated in FIG. 6, a set of the sheet-shaped members 50 and 50 is inverted at the opening in a state in which a pair of the extending parts 20 is held by the person in charge of the unclean field. More specifically, in a pair of the extending parts 20, the front and back of the sheet-shaped member 50 sandwiched between the thumbs inserted between a set of the sheet-shaped members 50 and 50 and the forefingers disposed outside the sheet-shaped members 50 are inverted, so that the front and back of the sheet-shaped members 50 in the vicinity of the opening are inverted. Consequently, in the vicinity of the opening, inner surfaces of the clean sheet-shaped members 50 that are not exposed to the outside world are exposed to the outside. In this state, the accommodating container 60 is hygienically extracted by the person in charge of the clean field.

Herein, in the present embodiment, the medical container 1 is configured to include the accommodation part 10 and a pair of the extending parts 20 extending outward in the width direction WD from the accommodation part 10. Consequently, it is possible to secure the long length in the width direction WD of the opening. Accordingly, a set of the sheet-shaped members 50 and 50 can be easily inverted at the opening by holding a pair of the extending parts 20 with both hands, and therefore the accommodating container 60 accommodated in the accommodation part 10 can be extracted in a state in which the inner surfaces of the uncontaminated sheet-shaped members 50 are exposed.

The length H1 in the height direction HD of each extending part 20 is made shorter than the length H2 in the height direction HD of the accommodation part 10. Further, the base sides of the extending parts 20 are inclined upward from the end portion in the width direction WD toward the accommodation part 10. Consequently, when the sheet-shaped members 50 are inverted at the opening, the extending parts 20 can be prevented from interfering with the accommodation part 10, and therefore the sheet-shaped members can be inverted smoothly.

when a set of the sheet-shaped members 50 and 50 is inverted at the opening, the sheet-shaped members 50 and 50 can be inverted with the upper end portions 30a of the partition joining parts 30 as bending starting points of the sheet-shaped members 50, and therefore a set of the sheet-shaped members 50 and 50 can be inverted more stably. That is, when the sheet-shaped members 50 are to be inverted at the opening, it is possible to prevent a set of the sheet-shaped members 50 and 50 from being bent together on one side in the thickness direction TD and closing the opening. The positions 30a of the upper end portions of the partition joining parts 30 are located on the lower end side with respect to the upper end portion 60a of the accommodating container 60 in the state in which the accommodating container 60 is accommodated in the accommodation part 10. Consequently, when the sheet-shaped members 50 are inverted at the opening, an end portion of the accommodating container 60 can be protruded from the opening. Accordingly, the accommodating container 60 can be extracted more easily and hygienically.

According to the medical container 1 of the first embodiment described above, the following effects are obtained.

(1) The medical container 1 is provided by joining together the rims of a set of the sheet-shaped members 50 and 50, and configured to include the accommodation part 10, and a pair of the extending parts 20 that is disposed on the one end side in the height direction HD of the accommodation part 10 and extends outward in the width direction WD from the accommodation part 10. Consequently, when the one end side in the height direction HD of the accommodating container 60 is opened with scissors or the like, and the accommodating container 60 accommodated in the medical container 1 is extracted, it is possible to secure the longer length in the width direction of the opening provided by opening with the scissors or the like. Accordingly, while a pair of the extending parts 20 are held with both hands, a set of the sheet-shaped members 50 and 50 can be easily inverted at the opening, and therefore the accommodating container 60 accommodated in the accommodation part 10 can be extracted in the state in which the inner surfaces of the uncontaminated sheet-shaped members 50 are exposed. As a result, the accommodating container 60 can be easily extracted without being contaminated. Further, in a pair of the extending parts 20, a set of the sheet-shaped members 50 and 50 is inverted by inserting fingers between a set of the sheet-shaped members 50 and 50, so that the fingers are not in contact with the accommodation part 10, and therefore the accommodating container 60 can be more hygienically extracted.

(2) The medical container 1 is configured to include the partition joining parts 30 that extend from the other end side to the one end side in the height direction HD and partition the accommodation part 10 and the extending parts 20. Consequently, when a set of the sheet-shaped members 50 and 50 is inverted at the opening, the end portions of the partition joining parts 30 can be inverted as the bending starting points of the sheet-shaped members 50, and therefore a set of the sheet-shaped members 50 and 50 can be inverted more stably. That is, when the sheet-shaped members 50 are to be inverted at the opening, a set of the sheet-shaped members 50 and 50 is prevented from being bent together on one side in the thickness direction TD and closing the opening. Further, when fingers are inserted between a set of the sheet-shaped members 50 and 50 in a pair of the extending parts 20 to invert a set of the sheet-shaped members 50 and 50, the inserted fingers are prevented from moving toward the accommodation part 10, and therefore the accommodating container 60 can be more hygienically extracted.

(3) The position 30a of the end portion (upper end portion) on the one end side in the height direction HD of each partition joining part 30 is located on the other end side (lower side) with respect to the one end portion (upper end portion) 60a in the height direction HD of the accommodating container 60 in the state in which the accommodating container 60 is accommodated in the accommodation part 10. Consequently, when the sheet-shaped members 50 are inverted at the opening, the end portion of the accommodating container 60 can be protruded from the opening. Accordingly, the accommodating container 60 can be extracted more easily and hygienically.

(4) The medical container 1 is configured to include the regulating joining parts 40 that regulate the position of the accommodating container 60 accommodated in the accommodation part 10. Consequently, even when the accommodation part 10 is made wider than the width of an accommodated object, the accommodating container 60 accommodated in the accommodation part 10 can be positioned. Therefore, when the accommodating container 60 is extracted, a tip of the accommodating container 60 is suitably protruded from the opening. Accordingly, it is possible to further improve the extractability of the accommodating container 60.

(5) The length H1 in the height direction HD of each extending part 20 is configured to be shorter than the length H2 in the height direction HD of the accommodation part 10. Consequently, the position on the other end side (lower end side) in the height direction HD of each extending part 20 can be made higher than the position on the other end side (lower end side) in the height direction HD of the accommodation part 10. Accordingly, when the sheet-shaped members 50 are inverted at the opening, the extending parts 20 can be less likely to interfere with the accommodation part 10, and therefore the sheet-shaped members 50 are inverted smoothly.

(6) The side on the other end side (lower end side) in the height direction HD of each extending part 20 is inclined on the one end side (upper end side) from the end portion in the width direction ND toward the accommodation part 10. Consequently, when the sheet-shaped members 50 are inverted at the opening, the extending parts 20 can be further less likely to interfere with the accommodation part 10, and therefore the sheet-shaped members 50 are inverted smoothly. The areas of the extending parts 20 can be sufficiently secured particularly on the outside in the width direction WD, and therefore when the sheet-shaped members 50 are inverted, the extending parts 20 can be firmly held by the thumbs and the forefingers. Accordingly, it is possible to improve operability when the sheet-shaped members 50 are inverted.

Figure 7:
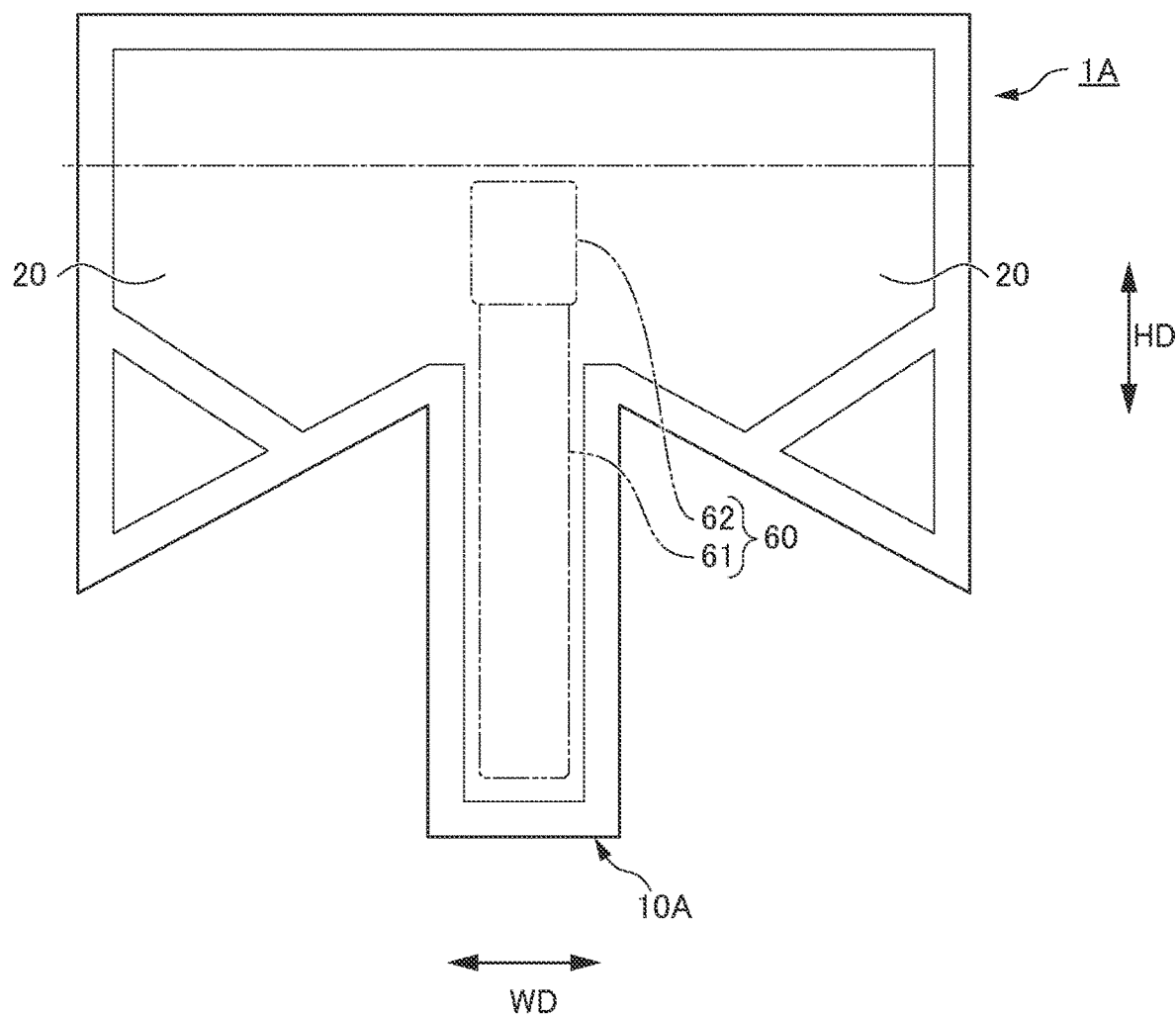
FIG. 7 is a plan view illustrating a medical container according to a second embodiment of the present invention, and is a plan view illustrating a state in which an accommodated object is accommodated in the medical container.

Now, a medical container 1A according to a second embodiment of the present invention will be described with reference to FIG. 7. In the description of the second embodiment, the same components are denoted by the same reference numerals, and the description thereof will be omitted or simplified. The medical container 1A of the second embodiment is different from the first embodiment mainly in that the medical container 1A does not include any partition joining part and any regulating joining part. In the medical container 1A of the second embodiment, as illustrated in FIG. 7, the length in the width direction WD of an accommodation part 10A is configured to be slightly larger than the width of an accommodating container 60 as an accommodated object. Consequently, the accommodating container 60 is accommodated in a state of being positioned in the accommodation part 10A. Further, in the second embodiment, when the medical container 1A is opened and the sheet-shaped members 50 are inverted at an opening, joining parts of boundary portions between the accommodation part 10A and extending parts 20 serve as bending starting points, and the sheet-shaped members 50 are inverted. According to the medical container 1A of the second embodiment, the above effects (1), (5) and (6) are obtained.

Now, a medical container 1B according to a third embodiment of the present invention will be described with reference to FIG. 8 to FIG. 10.

Figure 8:
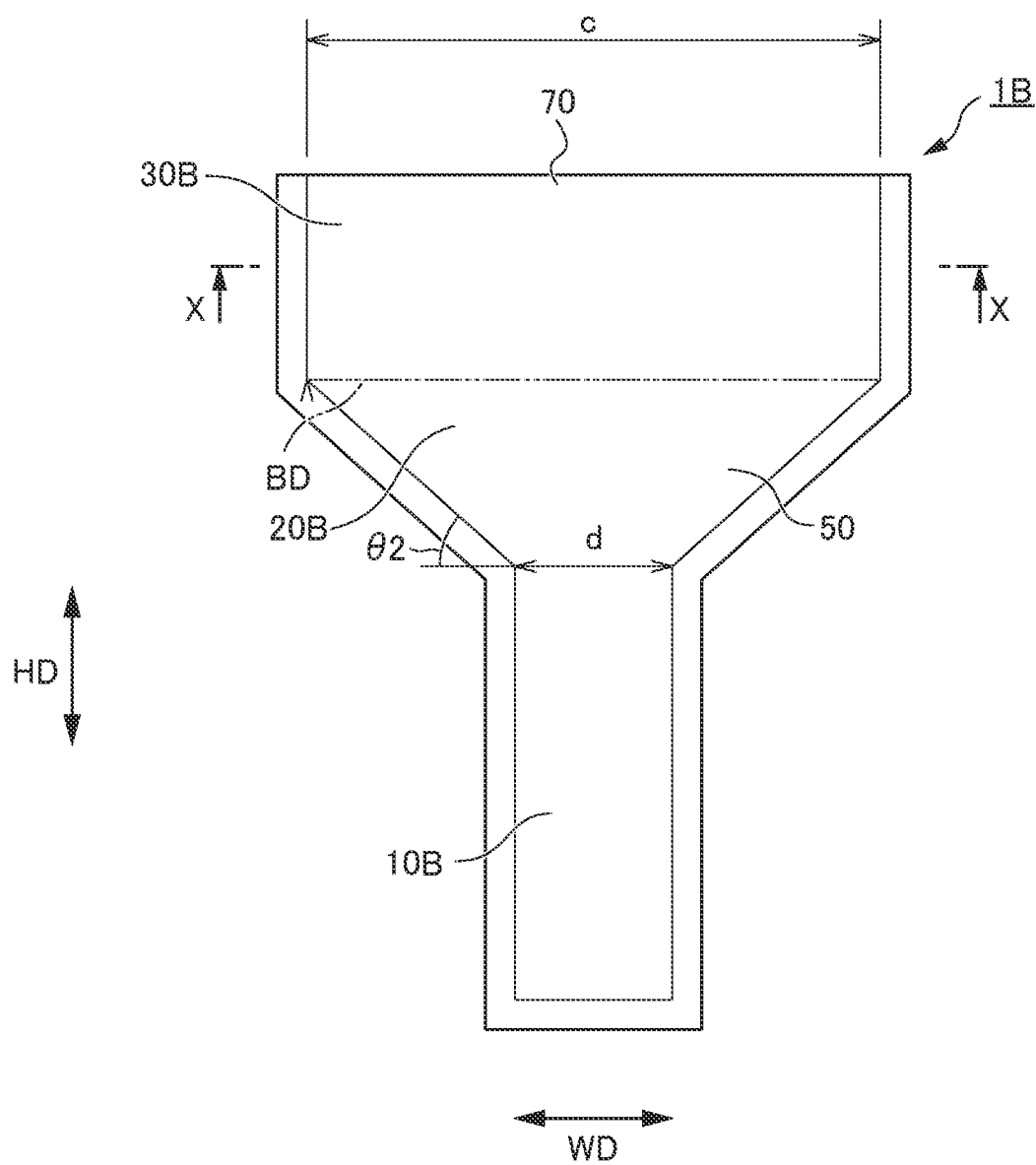
FIG. 8 is a plan view illustrating a medical container according to a third embodiment of the present invention.
Figure 9:
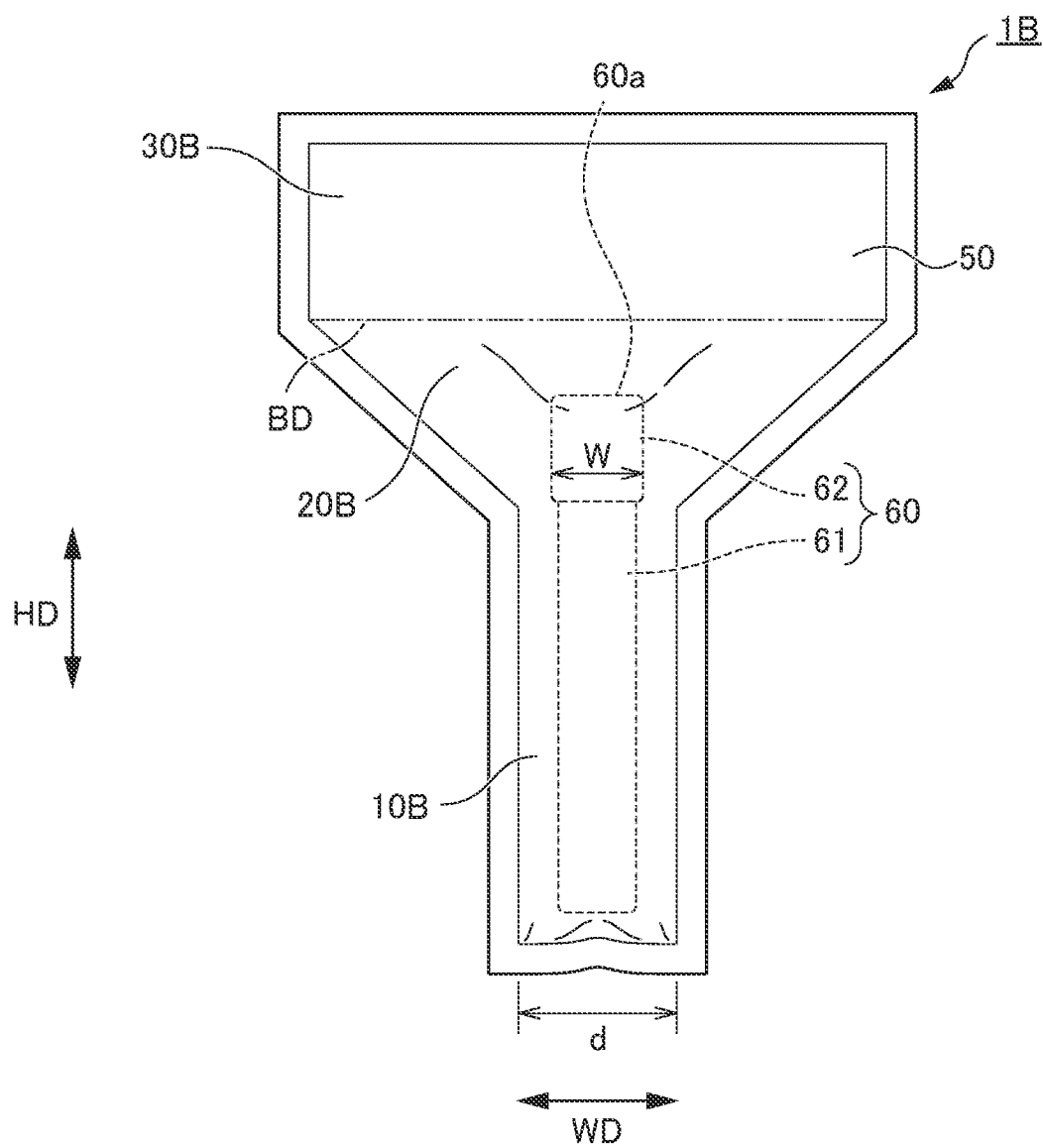
FIG. 9 is a plan view illustrating a state in which an accommodated object is accommodated in the medical container according to the third embodiment.
Figure 10:
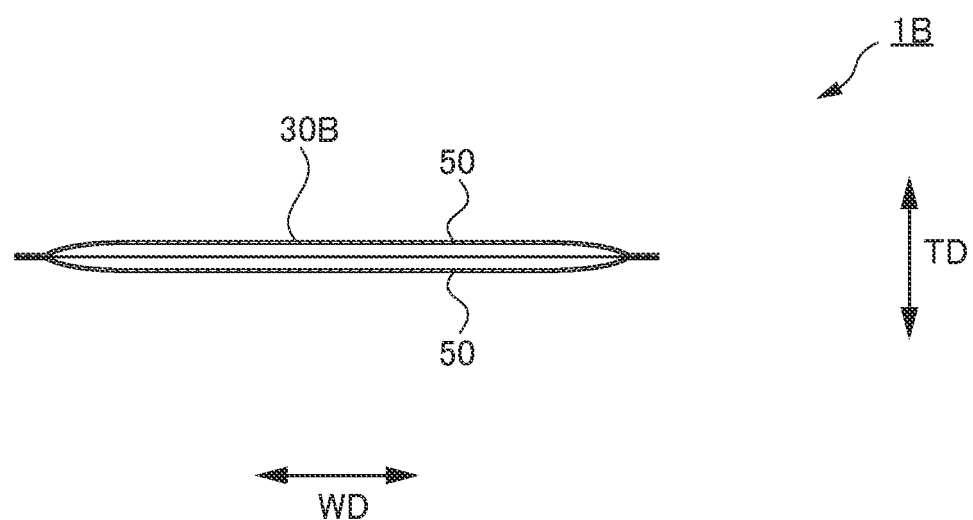
FIG. 10 is a cross-sectional view taken along a line X-X of FIG. 8.

As illustrated in FIG. 8 to FIG. 10, the medical container 1B is formed in a bag shape by joining together rims of a set (two) of sheet-shaped members 50 and 50 (see FIG. 10) disposed facing each other by heat sealing or ultrasonic joining except an accommodating opening 70 (upper side portion in FIG. 8) for accommodating an accommodated object.

As illustrated in FIG. 8 to FIG. 10, the medical container 1B includes an accommodation part 10B, an inclined part 20B, a rectangular part 30B, and the accommodating opening 70.

As illustrated in FIG. 8 and FIG. 9, the accommodation part 10B is formed in a rectangular shape in plan view in which the length d in the width direction WD (hereinafter, also referred to as the width d of the accommodation part 10B) is shorter than the length in the height direction HD, and is disposed at the central part in the width direction WD of the medical container 1B. The accommodation part 10B accommodates, as an accommodated object, an instrument, a pharmaceutical preparation, or the like used for medical treatment in a sterile state. In the present embodiment, as illustrated in FIG. 9, the accommodation part 10B accommodates a cylindrical accommodating container 60 that accommodates cells used for regenerative medicine. The accommodating container 60 includes a cylindrical main body 61 having an open one end side and a cap 62 detachably attached to the main body 61, and the cap 62 is accommodated in the accommodation part 10B so as to be located on the upper end side of a medical container 1 which is one end side in the height direction HD of the medical container 1. The width d of the accommodation part 10B may be configured to have a length into which the accommodating container 60 can be inserted. In the present embodiment, as illustrated in FIG. 9, the width d of the accommodation part 10B is set to be about twice the width W of the cap 62 of the accommodating container 60. Consequently, when the accommodating container 60 is inserted into the accommodation part 10B, the accommodating container 60 can be easily inserted. Herein, the accommodating container 60 is preferably set the length in the height direction HD of the accommodation part 10B so as to protrude from an upper end portion of the accommodation part 10B by about 10 mm to 15 mm, in a state in which the accommodating container 60 is accommodated in the accommodation part 10B. Consequently, the accommodating container 60 can be easily extracted from the accommodation part 10B.

In the present embodiment, the left-right direction in FIG. 8 is defined as the width direction WD of the medical container 1B, the direction that intersects the width direction WD and is along the plane direction of the sheet-shaped members 50 (vertical direction in FIG. 8) is defined as the height direction HD, and the overlapping direction of a set of the sheet-shaped members 50 and 50 (vertical direction in FIG. 10) is defined as the thickness direction TD.

The inclined part 20B is disposed on the one end side in the height direction HD of the accommodation part 10B (the upper end side of the accommodation part 10B). The inclined part 20B communicates with the accommodation part 10B, and is formed in a shape in which the length in the width direction WD becomes longer (wider) toward the one end side (upper side) in the height direction HD. The inclined part 20B has a pair of lateral sides that is inclined with respect to the height direction HD and extends on both sides in the width direction WD. In the inclined part 20B, a set of the sheet-shaped members 50 is joined together at a pair of the lateral sides, and a set of the sheet-shaped members 50 is not joined together at other portions. The length in the width direction WD of the inclined part 20B is configured to gradually increase from the accommodation part 10B toward the rectangular part 30B. The minimum width of the inclined part 20B is the same width as the width d of the upper end portion of the accommodation part 10B, and the maximum width is the same width as the width c of the rectangular part 30B. In the present embodiment, a pair of the lateral sides of the inclined part 20B is inclined at the same angle with respect to the height direction HD, and extends.

The rectangular part 30B is disposed on one end side (upper end side of the inclined part 20B) in the height direction HD of the inclined part 20B. In the rectangular part 30B, a set of the sheet-shaped members 50 is joined together on the lateral sides along the height direction HD, and a set of the sheet-shaped members 50 is not joined together at other portions. The length c in the width direction WD of the rectangular part 30B (hereinafter, also referred to as the width c of the rectangular part 30B) is configured to be larger than the width d of the upper end portion of the accommodation part 10B. Further, as will be described in detail later, when the accommodating container 60 is extracted, the medical container 1B is cut along the width direction WD in the vicinity of a boundary part BD with the inclined part 20B in the rectangular part 30B.

The accommodating opening 70 is provided without partially joining together rims of a set of sheet-shaped members 50. In the present embodiment, the accommodating opening 70 is provided over the entire length of the side on the one end side (upper end side) in the height direction, that is, the side on the upper end side of the rectangular part 30B.

The medical container 1B of the present embodiment described above is used as follows.

When the accommodating container 60 is accommodated in the medical container 1B, the accommodating container 60 accommodating cells is accommodated, from the accommodating opening 70, in the medical container 1B in which all sides except an upper side, which is the side on the one end side in the height direction HD and is provided with the accommodating opening 70, are joined together. Herein, the accommodating container 60 accommodated in the accommodation part 10B such that the cap 62 is located on the upper end side. Thereafter, the upper side of the medical container 1B is joined together, and the accommodating container 60 is accommodated in the medical container 1B in a sealed state. In this state, an upper end portion 60a of the accommodating container 60 is located on the lower end side with respect to the boundary part BD between the rectangular part 30B and the inclined part 20B, that is, inside the inclined part 20B (see FIG. 9).

The cells accommodated in the accommodating container 60 are accommodated in the medical container 1B and cryopreserved in the sealed state until the cells are used.

When the cells accommodated in the accommodating container 60 are used, the cells are transported to an operating room or the like in which an unclean field and a clean field are separated in a state of being accommodated in the medical container 1B. Then, the medical container 1B is opened by a person in charge of the unclean field, and the accommodating container 60 is extracted from the medical container 1B by a person in charge of the clean field.

In the medical container 1B of the present embodiment, the shape of the inclined part 20B is properly set, so that it is possible to easily invert the inclined part 20B after cutting.

Figure 11:
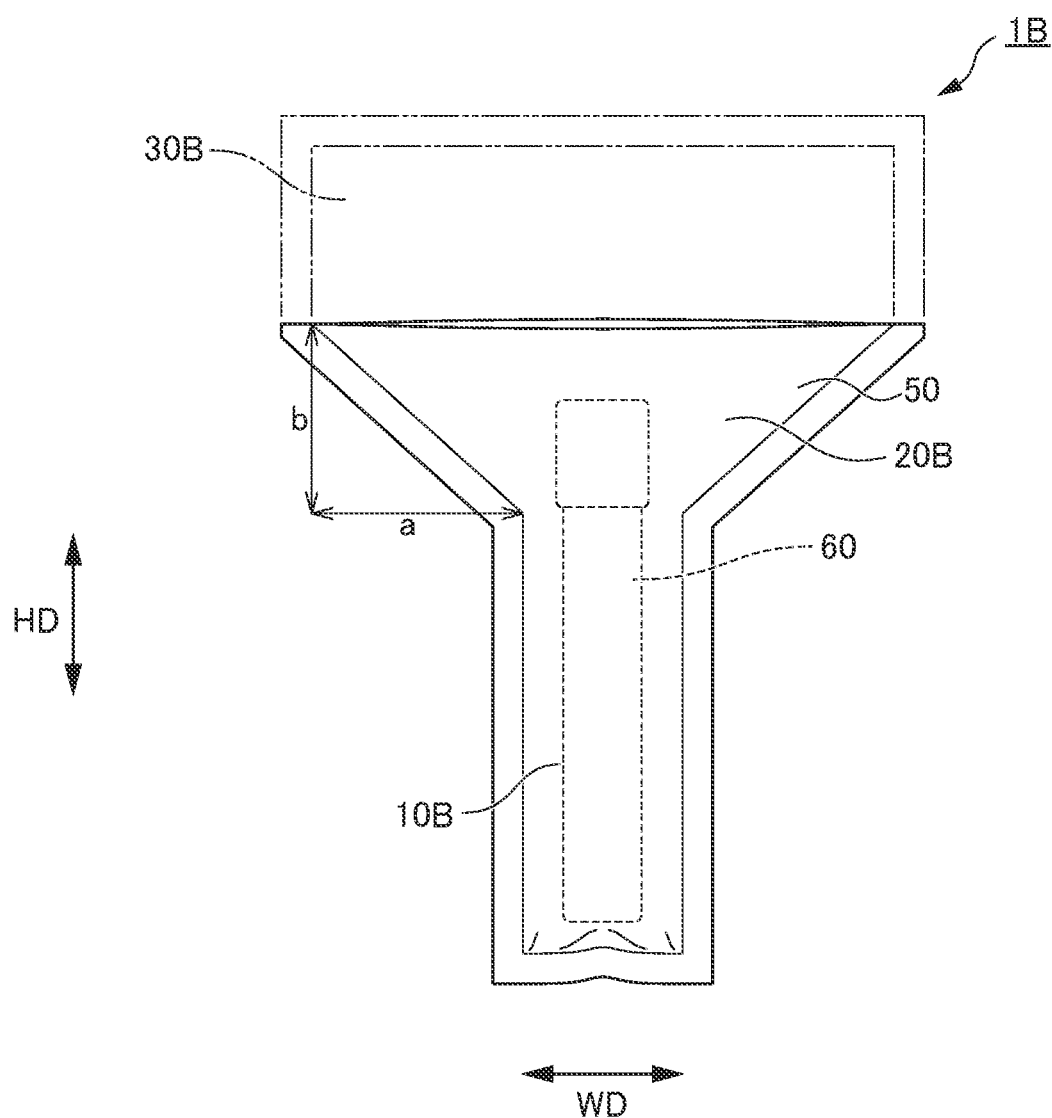
FIG. 11 is a diagram illustrating a method of using the medical container according to the third embodiment, and is a diagram illustrating a state in which an upper end portion of the medical container is cut and opened.

A procedure for extracting the accommodating container 60 from the medical container 1B will be described with reference to FIG. 11 to FIG. 13. First, as illustrated in FIG. 11, the person in charge of the unclean field cuts a predetermined cutting position of the medical container 1B with scissors or the like. Consequently, an opening for extraction is provided on the upper side of the medical container 1B. Herein, the medical container 1B is preferably cut in the vicinity of the boundary part BD with the inclined part 20B in the rectangular part 30B (see FIG. 8 and FIG. 9). In the present embodiment, the shape of the inclined part 20B is set such that the distance b in the height direction HD between the upper end portion of the accommodation part 10B and the boundary part BD is 20 mm or more and 40 mm or less. The distance b is set to 20 mm or more, so that it is possible to prevent scissors or the like from touching the upper end portion 60a of the accommodating container 60 when cutting the rectangular part 30B in the vicinity of the boundary part BD.

Figure 12:
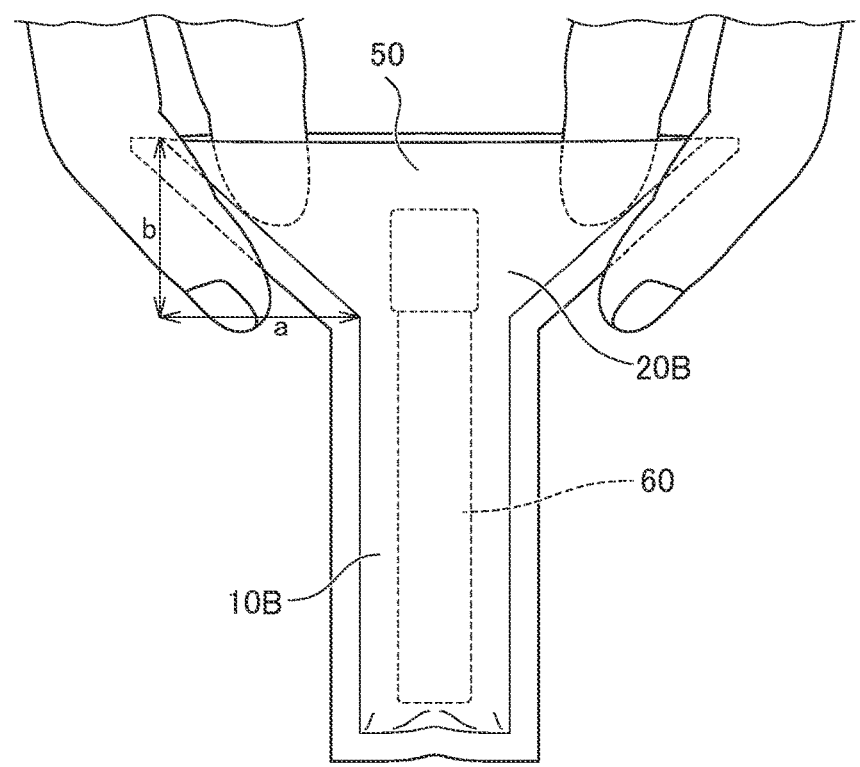
FIG. 12 is a diagram illustrating a method of using the medical container according to the third embodiment, and is a diagram illustrating a state of holding an inclined part.

Next, as illustrated in FIG. 12, the inclined part 20B is held by the person in charge of the unclean field. Herein, in the inclined part 20B, a set of the sheet-shaped members 50 is not joined together except for the rim parts (sides), and therefore the person in charge of the unclean field inserts, for example, his/her thumbs into the inclined part 20B from the opening, and sandwiches the sheet-shaped members 50 between the inserted thumbs and his/her forefingers, so that it is possible to hold the inclined part 20B Herein, a distance a in the width direction WD between an end portion of the upper end portion of the accommodation part 10B and an end portion of the rectangular part 30B is made to be 35 mm or more, so that the person in charge of the unclean field can insert his/her thumbs of his/her both hands into the inclined part 20B without touching the accommodating container 60.

Figure 13:
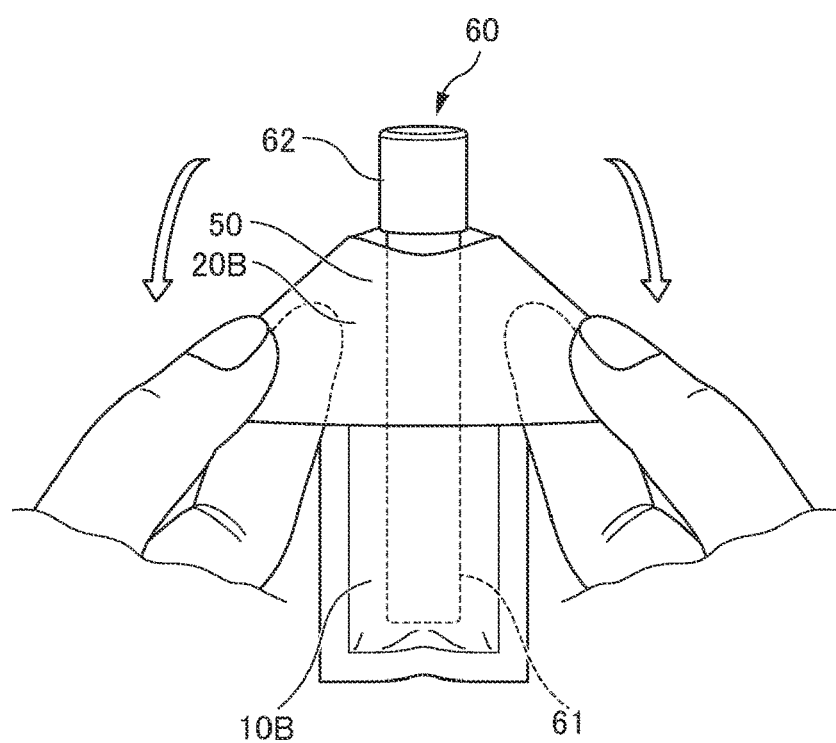
FIG. 13 is a diagram illustrating a method of using the medical container according to the third embodiment, and is a diagram illustrating a state in which a set of sheet-shaped members is inverted at an opening while holding an inclined part.

Then, as illustrated in FIG. 13, a set of the sheet-shaped members 50 and 50 is inverted at the opening in a state in which the inclined part 20B is held by the person in charge of the unclean field. More specifically, in the inclined part 20B, the front and back of the sheet-shaped members 50 sandwiched between the thumbs inserted between a set of the sheet-shaped members 50 and 50 and the forefingers disposed outside the sheet-shaped members 50 are inverted, so that the front and back of the sheet-shaped members 50 in the vicinity of the opening are inverted. Consequently, in the vicinity of the opening, inner surfaces of the clean sheet-shaped members 50 that are not exposed to the outside world are exposed to the outside. In this state, the accommodating container 60 is hygienically extracted by the person in charge of the clean field.

Herein, the distance a between the end portion of the upper end portion of the accommodation part 10B and the end portion of the rectangular part 30B is made to be 70 mm or less, and the distance b between the upper end portion of the accommodation part 10B and the boundary part BD (the upper end portion of the inclined part 20B) is made to be 40 mm or less, so that a position in the height direction HD where the inclined part 20B is inverted can be brought closer to the upper end portion of the accommodation part 10B. Accordingly, the inverted position in the inclined part 20B is lower than the upper end portion 60a of the accommodating container 60, and therefore it is possible to increase an exposed portion of the upper end portion of the accommodating container 60 from the medical container 1B, and the person in charge of the clean field can easily extract the accommodating container 60. When the distance a exceeds 70 mm, finger grip portions of the inclined part 20B and the sheet-shaped member 50 portions in a vicinity portion thereof can be easily inverted, but it becomes difficult to invert the opening side at the central portion in the width direction WD, which is a portion for extracting the accommodating container 60. As a result, it becomes difficult to set the inverted position to an appropriate position. Further, when the distance b exceeds 40 mm, it becomes difficult to invert the inclined part 20B, which is not preferable. That is, the distance a between the end portion of the upper end portion of the accommodation part 10B and the end portion of the rectangular part 30B is 70 mm or less, and the distance b between the upper end portion of the accommodation part 10B and the boundary part BD (the upper end portion of the inclined part 20B) is 40 mm or less, so that the accommodating container 60 can be easily inverted at the appropriate position, and it is possible to increase the exposed portion of the upper end portion of the accommodating container 60 from the medical container 1 in the inverted state, and therefore it is possible to easily extract the accommodating container 60.

In the present embodiment, as described above, the cutting position for opening the medical container 1B is set to the vicinity of the boundary part BD with the inclined part 20B in the rectangular part 30B, so that it is possible to easily invert the inclined part 20B compared to a case where the rectangular part 30B is cut above the vicinity of the boundary part BD. A mark for indicating the cutting position for opening may be given to the medical container 1B. Examples of the mark for indicating the cutting position include a display attached to the sheet-shaped members 50 along the cutting position, a notch provided on the side portion of the rectangular part 30B, or the like.

According to summarization of a result examined by the present inventor, it is found that when the distance a in the width direction WD between the end portion of the upper end portion of the accommodation part 10B and the end portion of the rectangular part 30B is 35 mm or more and 70 mm or less, and when the distance b in the height direction HD between the upper end portion of the accommodation part 10B and the boundary part BD with the accommodation part 10B (the upper end portion of the inclined part 20B) is 20 mm or more and 40 mm or less, the inclined part 20B is easily inverted after cutting the medical container 1B at the boundary part BD.

In addition, the present inventor further examined the preferable shape of the inclined part 20B for easily inverting the inclined part 20B from various viewpoints. As a result, it is found that the length d (accommodation part 10B) in the width direction WD of the accommodation part 10B is not preferably more than the distance a in the width direction WD between the end portion of the upper end portion of the accommodation part 10B and the end portion of the rectangular part 30B, and the length c in the width direction WD of the rectangular part 30B (width of the rectangular part 30B) is preferably 200 mm or less, and the angle θ2 on the acute angle side with respect to the width direction WD of the lateral side of the inclined part 20B is 20° or more and 40° or less.

According to the medical container 1 of the embodiment described above, the following effects are obtained.

(7) The medical container 1B is provided by joining together the rims of a set of sheet-shaped members 50 and 50, and is configured to include the accommodation part 10B, the inclined part 20B disposed on the upper end side in the height direction HD of the accommodation part 10B, and the rectangular part 30B disposed on the upper end side in the height direction of this inclined part 20B, and the inclined part 20B is configured such that the width gradually decreases from the upper end side to the lower end side, the distance a in the width direction WD between the end portion of the upper end portion of the accommodation part 10B and the end portion of the upper end portion of the inclined part 20B is set to 35 mm or more and 70 mm or less, and the distance b in the height direction HD between the upper end portion of the accommodation part 10B and the boundary part BD is set to 20 mm or more and 40 mm or less. Consequently, when the one end side in the height direction HD of the medical container 1B is opened with scissors or the like and the accommodating container 60 accommodated in the medical container 1B is extracted, the medical container 1B is cut in the vicinity of the boundary part BD between the rectangular part 30B and the inclined part 20B, so that a set of the sheet-shaped members 50 and 50 can be easily inverted by holding the inclined part 20B with both hands. Accordingly, the accommodating container 60 accommodated in the accommodation part 10B can be extracted in a state in which inner surfaces of the uncontaminated sheet-shaped members 50 are exposed. Accordingly, the inverted position in the inclined part 20B can be set to the vicinity of the accommodation part 10B, and therefore the accommodating container 60 can be easily extracted. Further, when cutting, it is possible to prevent scissors or the like from touching the upper end portion 60a of the accommodating container 60. As a result, the accommodating container 60 can be easily extracted without being contaminated. Further, when fingers are inserted between a set of the sheet-shaped members 50 and 50 in the inclined part 20B, and a set of the sheet-shaped members 50 and 50 is inverted, so that the inserted fingers are prevented from touching the accommodation part 10B, and therefore the accommodating container 60 can be more hygienically extracted.

(8) The width d of the upper end portion of the accommodation part 10B is set to at most the distance a between the end portion of the upper end portion of the accommodation part 10B and the end portion of the rectangular part 30B. Consequently, the force of the fingers when the fingers are put into the inclined part 20B and the inclined part 20B is inverted is easily transmitted to the inclined part 20B, and therefore the inclined part 20B can be inverted more easily.

(9) The width of the rectangular part 30B is set to be 200 mm or less. Consequently, the inverted position in the inclined part 20B can be set to the vicinity of the accommodation part 10B, and therefore the accommodating container 60 can be easily extracted.

(10) The angle θ2 on the acute angle side with respect to the width direction WD of the lateral side of the inclined part 20B is set to be 20° or more and 40° or less. Consequently, a set of the sheet-shaped members 50 and 50 can be easily inverted by holding the inclined part 20B with both hands.

EXAMPLES

Example 1

Next, as to the medical container 1B of the present embodiment, medical containers obtained by variously changing the distance a between the end portion of the upper end portion of the accommodation part 10B and the end portion of the upper end portion of the inclined part 20B, and the distance b between the upper end portion of the accommodation part 10B and the boundary part BD (the upper end portion of the inclined part 20B) were prepared as test specimens, and the ease of inversion was evaluated. The width d of the accommodation part 10B was set to 27 mm. The results are illustrated in Table 1, and the relationship between the distance a and the distance b is illustrated in Table 2 by the angle θ2 on the acute angle side with respect to the width direction WD of the lateral side of the inclined part 20B. As the sheet-shaped member constituting the medical container 1B used in the examples, a sheet having a thickness of 0.35 mm made of EVA resin was used. As to the ease of inversion in Table 1, while one that can be inverted without putting fingers all the way into the inclined part 20B and does not have any feeling of resistance is defined as "very good" (indicated by bullseye symbol (⊙)), one that can be inverted without putting fingers all the way into the inclined part 20B but has a feeling of resistance is defined as "good" (indicated by circle symbol (○)), one that can be inverted by putting fingers all the way into the inclined part 20B but has a feeling of resistance is defined as "fair" (indicated by triangle symbol 1 (Δ1)), one that can be inverted in the vicinity of a finger gripping point but cannot be smoothly inverted at a central part (opening) provided with the accommodation part accommodated in the accommodating container is defined as "poor" (indicated by triangle symbol 2 (Δ2)), and one that cannot be inverted is defined as "very poor" (indicated by cross symbol (x)), evaluation was performed on a five level scale. Examples that fall within the scope of the present invention are surrounded by a thick frame in each of Table 1 and Table 2.

TABLE 1

|  |  |  | Distance a (mm) | | | | | | | |
|---|---|---|---|---|---|---|---|---|---|---|
|  |  |  | Out of Range | | | | Within Range | | | Out of Range |
| Ease of Inversion | | | 26.5 | 29.0 | 31.5 | 34.0 | 41.5 | 51.5 | 61.5 | 71.5 |
| Distance b (mm) | Within Range | 23 | Δ1 | Δ1 | ○ | ○ | ◎ | ◎ | ◎ | Δ2 |
|  |  | 30 | x | x | Δ1 | Δ1 | ◎ | ◎ | ◎ | Δ2 |
|  |  | 37 | x | x | Δ1 | ○ | ◎ | ◎ | ◎ | Δ2 |
|  | Out of Range | 50 | x | x | x | x | Δ1 | ○ | ○ | Δ2 |

TABLE 2

|  |  |  | Distance a (mm) | | | | | | | |
|---|---|---|---|---|---|---|---|---|---|---|
|  |  |  | Out of Range | | | | Within Range | | | Out of Range |
| Angle θ2 | | | 26.5 | 29.0 | 31.5 | 34.0 | 41.5 | 51.5 | 61.5 | 71.5 |
| Distance b (mm) | Within Range | 23 | 41.0 | 38.4 | 36.1 | 34.1 | 29.0 | 24.1 | 20.5 | 17.8 |
|  |  | 30 | 48.5 | 46.0 | 43.6 | 41.4 | 35.9 | 30.2 | 26.0 | 22.8 |
|  |  | 37 | 54.4 | 51.9 | 49.6 | 47.4 | 41.7 | 35.7 | 31.0 | 27.4 |
|  | Out of Range | 50 | 62.1 | 59.9 | 57.8 | 55.8 | 50.3 | 44.2 | 39.1 | 35.0 |

According to Table 1, it can be found that in the range where the upper distance a of the accommodating container 60 is 35 mm or more and 70 mm or less and the distance b is 20 mm or more and 40 mm or less, the ease of inversion is "very good" (indicated by bullseye symbol (◎)), and the inversion can be easily performed. It can be confirmed that the angle θ2 within the range of the present invention of the distance a and the distance b is about 20° or more and 40° or less.

Example 2

Next, under the same conditions as in Example 1, while the distance at which the accommodating container 60 protrudes upward from the upper end portion of the accommodation part 10B is made constant (in present embodiment, the distance at which the accommodating container 60 protrudes is 10 mm), the ease of extraction of an accommodated object after inverting the inclined part 20B was evaluated. The results are illustrated in Table 3. While one that can be extracted with almost no finger into the accommodation part 10 is defined as "good" (indicated by circle symbol (○)), one that can be extracted by putting fingers into the accommodation part 10 is defined as "fair" (indicated by triangle symbol (Δ)), and one that cannot be extracted unless the finger is pushed all the way or cannot be extracted is defined as "poor" (indicated by cross symbol (x)), evaluation was performed on a three level scale. However, as to samples with low evaluations ("fair" (indicated by triangle symbol (Δ1)), "poor" (indicated by triangle symbol (Δ2)) and "very poor" (indicated by cross symbol (x))) in Table 1 (Example 1), evaluation for extraction in Example 2 was not performed, and the samples were evaluated as unevaluated (–). Examples that fall within the scope of the present invention are surrounded by a thick frame in Table 3.

TABLE 3

|  |  |  | Distance a (mm) | | | | | | | |
|---|---|---|---|---|---|---|---|---|---|---|
|  |  |  | Out of Range | | | | Within Range | | | Out of Range |
| Ease of Extraction | | | 26.5 | 29 | 31.5 | 34 | 41.5 | 51.5 | 61.5 | 71.5 |
| Distance b (mm) | Within Range | 23 | — | — | ○ | ○ | ○ | ○ | ○ | — |
|  |  | 30 | — | — | — | — | ○ | ○ | ○ | — |
|  |  | 37 | — | — | — | Δ | ○ | ○ | ○ | — |
|  | Out of Range | 50 | — | — | — | — | — | Δ | Δ | — |

According to Table 3, it has been found that in the range where the distance a is 35 mm or more and 70 mm or less and the distance b is 20 mm or more and 40 mm or less, the ease of extraction is "good" (indicated by circle symbol (○)), and the accommodating container 60 can be easily extracted. Even when the distance a was within the above range (35 mm to 70 mm), when the distance b was 50 mm or more, as illustrated in Table 1, the inverting property was not bad

[Sample example (a: 51.5 mm, b: 50 mm), (a: 61.5 mm, b: 50 mm)], but the inverted position where the inclined part 20E was inverted was located above the upper portion of the accommodating container 60, and therefore it was necessary to insert fingers to extract the accommodating container 60. Therefore, the evaluation for extraction was "fair" (indicated by triangle symbol (Δ)). On the contrary, in one having the distance a which was out of the range [sample example (a: 34 mm, b: 37 mm)] even when the distance b was within the range (20 mm to 40 mm), the evaluation of the inverting property in Table 1 was not bad. However, as in the above, the inversion position was located above the upper portion of the accommodating container, and therefore the evaluation of extractability was "fair" (indicated by triangle symbol (A)). In addition, two examples [sample examples (a: 31.5 mm, b: 23 mm), (a: 34.0 mm, b: 23 mm)] of a case where the distance a was smaller than 35 mm were not bad in extractability, but the evaluation of the inverting property in Table 1 was not "very good" (indicated by bullseye symbol (⊙)), and therefore the two examples were out of the range as comprehensive evaluation in which the extractability was added to the inverting property.

Example 3

Figure 14:
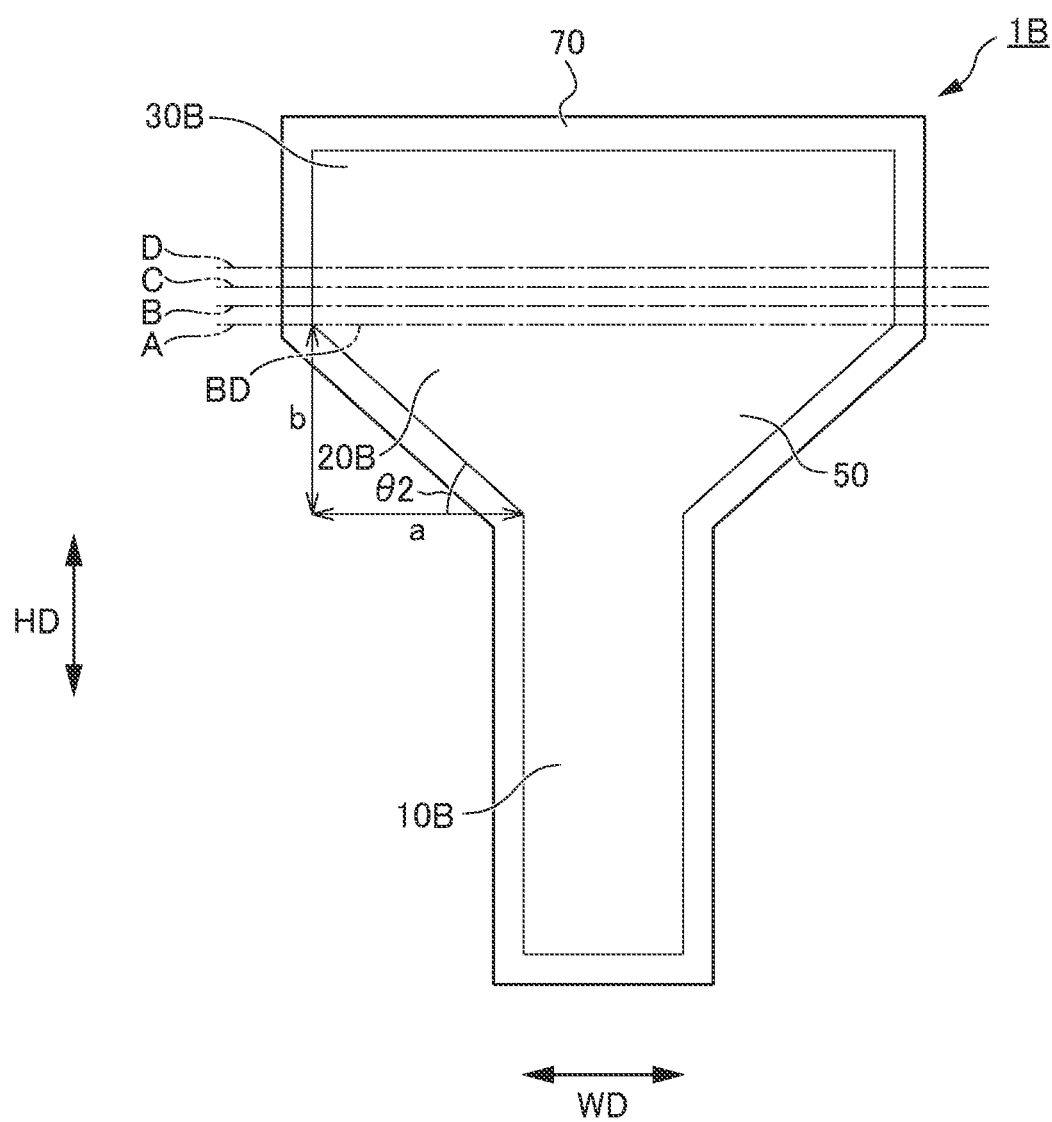
FIG. 14 is a diagram for illustrating a cutting position in Example 3 of the present invention.

Next, the ease of inversion in a case where the position where the medical container 1B was cut was changed when the accommodating container 60 was extracted was evaluated. As the conditions of the inclined part 20B, the distance a was set to 41.5 mm, the distance b was set to 27 mm, the angle θ was 33°, and the width d of the accommodation part 10B was set to 27 mm, and four test specimens were prepared. As illustrated in FIG. 14, the boundary part BD of the inclined part 20B and the rectangular part 30B was set to a line A, and lines B to D were set every 7 mm above the line A. A test specimen prepared on each line was cut and evaluated for ease of inversion. As a result, it was possible to easily invert the inclined part of the one cut along each of the lines A to C, but it was difficult to invert the inclined part of the one cut along the line D.

Although the preferred embodiments of the medical container of the present invention are described above, the present invention is not limited to the above embodiments and can be changed as appropriate. For example, in each of the first to third embodiments, the accommodating container 60 accommodating cells is accommodated as an accommodated object. However, the present invention is not limited to this. That is, an instrument used for medical treatment such as tweezers may be accommodated as an accommodated object.

Further, in each of the first to third embodiments, the accommodating opening 70 is provided over the entire length of the upper side of the medical container 1. However, the present invention is not limited to this. That is, the accommodating opening may be provided only at a portion corresponding to the accommodation part on the upper side of the medical container, and portions corresponding to the extending parts on the upper side may be joined together. Consequently, the opening length of the accommodating opening can be shortened, and therefore it is possible to reduce the risk of contamination inside the medical container when an accommodated object is accommodated.

Figure 15:
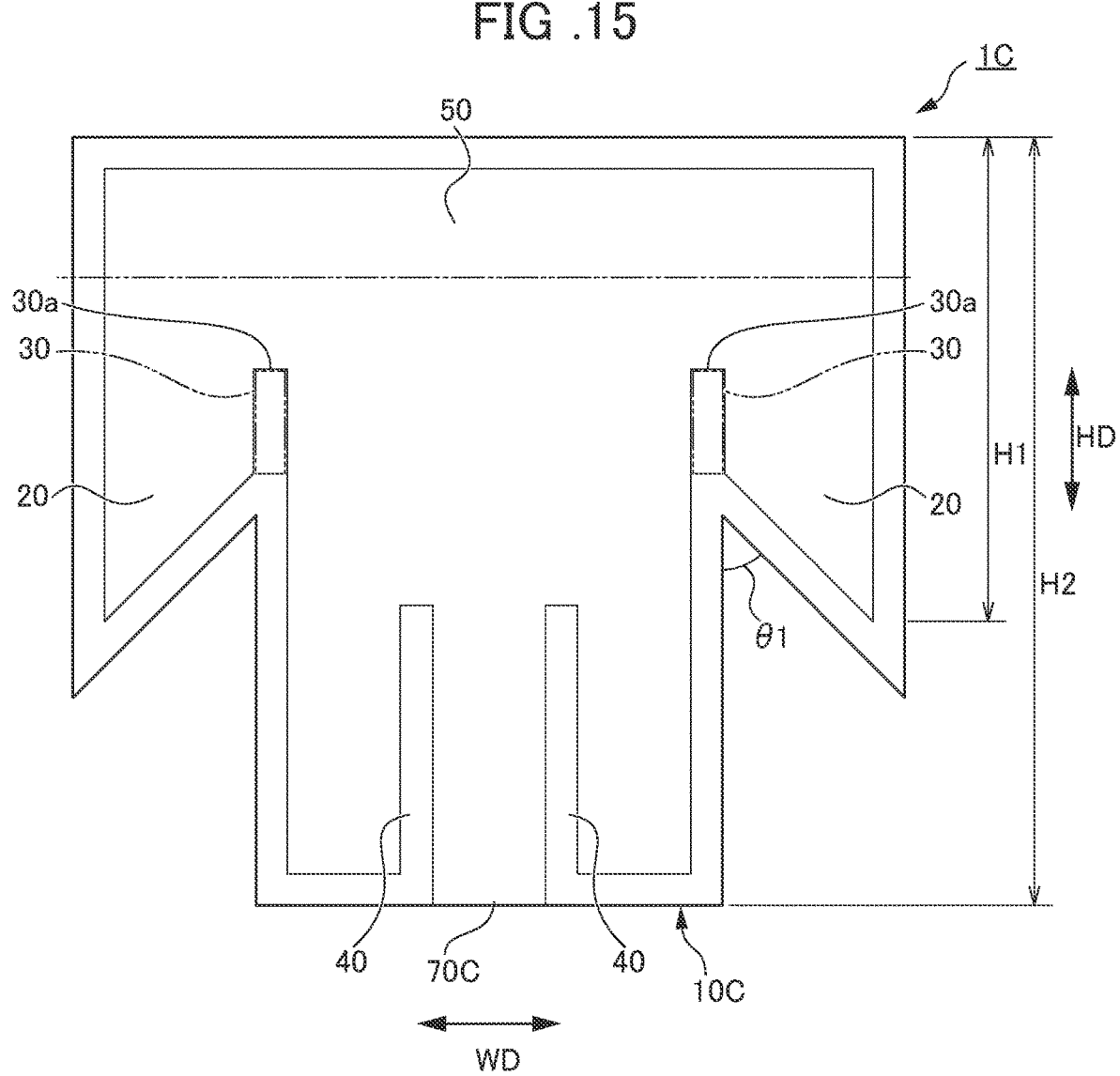
FIG. 15 is a plan view illustrating a modification of an accommodating opening in the medical container according to the first embodiment.

Further, as illustrated in FIG. 15, an accommodating opening 70C may be provided on the lower side of a medical container 1C (side on the other end side in the height direction HD). In this case, the accommodating opening 70C may be provided only in a portion between a pair of regulating joining parts 40 on the lower side. The accommodating opening 70C is provided on the lower side of the medical container 10, so that an accommodated object can be easily disposed in an accommodation part 10C (between a pair of the regulating joining parts 40). Further, the accommodating opening 70C is provided only in the portion between a pair of the regulating joining parts 40, so that the opening length of the accommodating opening 700 can be further shortened, and therefore it is possible to further reduce the risk of contamination inside the medical container 1C in the state of accommodating the accommodated object. In this case, the accommodating opening may be provided over the entire length of the lower side of the accommodation part ICC.

Figure 16:
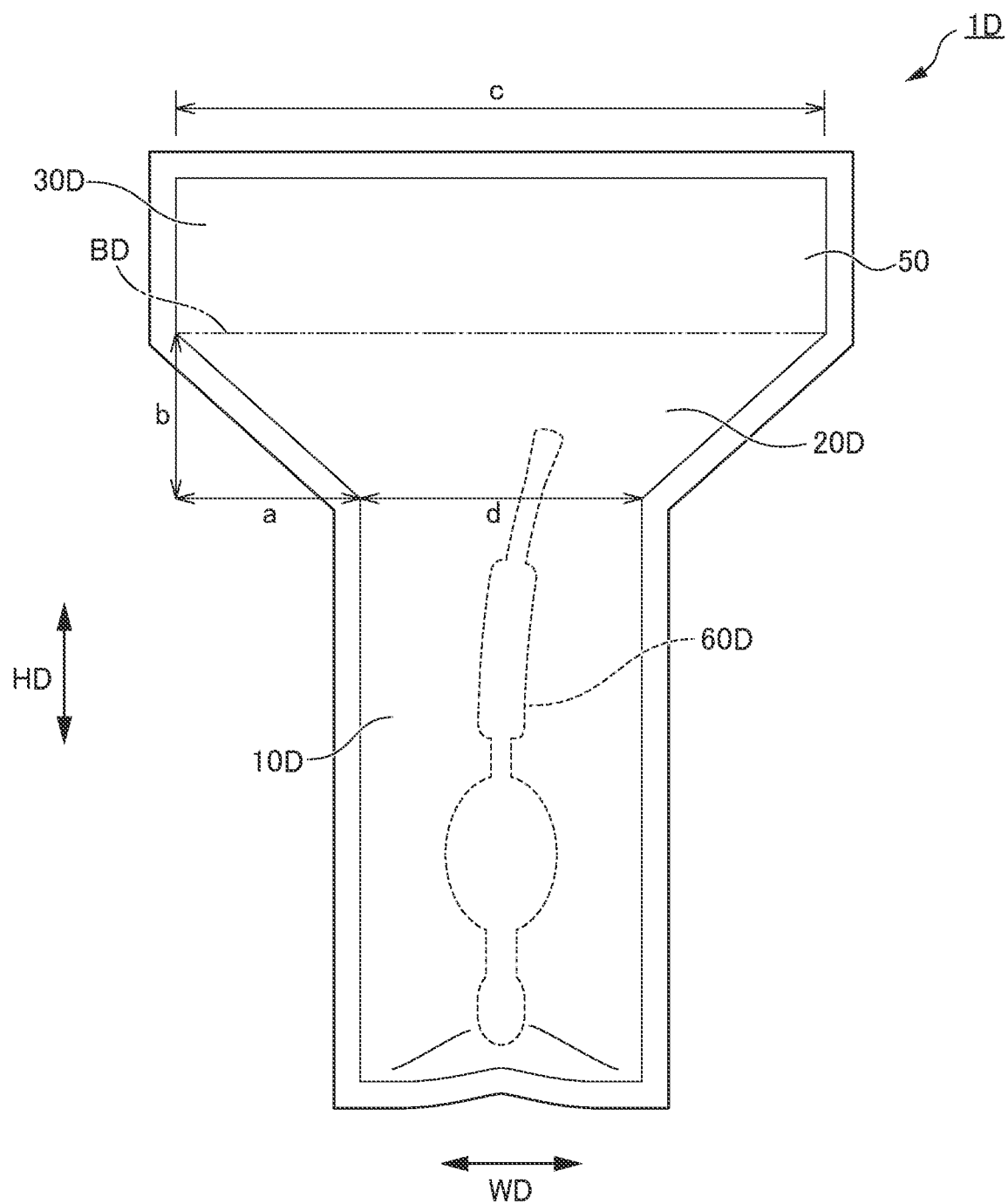
FIG. 16 is a plan view illustrating a modification of the width of the upper end portion of the accommodation part in the medical container according to the third embodiment.

In the third embodiment, an example in which the width d of the upper end portion of the accommodation part 10B is smaller than the distance a in the width direction WD between the end portion of the upper end portion of the accommodation part 10B and the end portion of the rectangular part 30B is illustrated. However, the present invention is not limited to this. For example, as in a medical container 1D illustrated in FIG. 16, the width d of an upper end portion of an accommodation part 10D may be larger than a distance a in the width direction WD between the end portion of the upper end portion of the accommodation part 10D and an end portion of a rectangular part 30D. Consequently, an accommodated object 60D having a large width can be accommodated.

Further, the shape of the accommodation part 10B is a rectangular shape extending in the height direction HD in the third embodiment, but the shape is not limited to this. The accommodation part may be formed in such a shape as to be able to accommodate according to the shape of the desired accommodating container. Further, the case where the size in the height direction HD of the accommodation part 10B is smaller than the length of the accommodating container 60 is described, but the present invention is not limited to this. That is, the accommodation part may be configured such that the entire accommodating container 60 is accommodated in the accommodation part. In this case, a person in charge of the unclean field lifts the lower portion of the accommodation part, so that the accommodating container 60 can be protruded from the accommodation part 10. Thus, the person in charge of the clean field can easily extract the accommodating container 60.

EXPLANATION OF REFERENCE NUMERALS 1, 1A, 1B, 1C, 1D medical container
10, 10A, 10B, 10C, 10D accommodation part
20 extending part
20B, 20D inclined part
30 partition joining part
30B, 30D rectangular part
40 regulating joining part
50 seal member
60 accommodating container (accommodated object)
70, 70C accommodating opening

The invention claimed is:
1. A medical container provided by joining together rims of a set of sheet-shaped members disposed facing each other, the medical container comprising:
   a bag having joined lateral sides, a joined bottom side and an opening;
   an accommodation part disposed at a central part in a width direction;

a pair of extending parts disposed on an upper end side in a height direction of the accommodation part, wherein the pair of extending parts is disposed on opposite sides in the width direction of the accommodation part, and each of the pair of extending parts extends outward in the width direction from the accommodation part; and partition joining parts that are provided at boundary portions between the accommodation part and the pair of extending parts, and each extends from a lower end side to an upper end side in the height direction to partially partition the accommodation part and the pair of extending parts, wherein the partition joining parts extend a portion of the space between the joined bottom side and the opening;

wherein the accommodation part and the pair of extending parts communicate on the upper end side in the height direction of the accommodation part above the partition joining parts.

2. The medical container according to claim 1, further comprising an accommodating opening provided in a portion of the rims.

3. The medical container according to claim 1, further comprising a regulating joining part that regulates a position of an accommodated object accommodated in the accommodation part, in the accommodation part.

4. A medical container provided by joining together rims of a set of sheet-shaped members disposed facing each other, the medical container comprising:

an accommodation part disposed at a central part in a width direction; and a pair of extending parts disposed on an upper end side in a height direction of the accommodation part, wherein the pair of extending parts is disposed on opposite sides in the width direction of the accommodation part, and each of the pair of extending parts extends outward in the width direction from the accommodation part, wherein a length in a height direction of each of the extending parts is shorter than a length in the height direction of the accommodation part, and the pair of extending parts each comprises a bottom portion which is inclined toward an upper end side in the height direction of each of the extending parts from an end portion of each of the pair of extending parts toward the accommodation part.

5. A medical container provided by joining together rims of a set of sheet-shaped members disposed facing each other, the medical container comprising:

an accommodation part disposed at a central part in a width direction;

an inclined part that is disposed on an upper end side in a height direction of the accommodation part, has a length in a width direction which becomes longer toward an upper side from the accommodation part, and is in communication with the accommodation part; and a rectangular part that is disposed on an upper end side in a height direction of the inclined part, has a length in the width direction which is equal to a length of an upper end portion of the inclined part, and is in communication with the inclined part, wherein a distance a in the width direction between an end portion of an upper end portion of the accommodation part and an end portion of an upper end portion of the inclined part is 35 mm or more and 70 mm or less, a distance b in a height direction between the upper end portion of the accommodation part and the upper end portion of the inclined part is 20 mm or more and 40 mm or less, and the rectangular part and the inclined part have a position of a boundary portion which is located closer to an upper end side than an upper end portion of an accommodated object in a state in which the accommodated object is accommodated in the accommodating part.

6. The medical container according to claim 5, wherein a width d of the upper end portion of the accommodation part is equal to or less than the distance a.

7. The medical container according to claim 5, wherein a width c of the upper end portion of the inclined part is 200 mm or less.

8. The medical container according to claim 5, wherein an angle θ2 on an acute angle side with respect to the width direction of a lateral side of the inclined part is 20° or more and 40° or less.

* * * * *